United States Patent [19]

Lee et al.

[11] Patent Number: 4,798,789

[45] Date of Patent: Jan. 17, 1989

[54] CDNA CLONES CODING FOR POLYPEPTIDES EXHIBITING MURINE INTERLEUKIN-2 ACTIVITY

[75] Inventors: Frank D. Lee; Takashi Yokota; Ken-ichi Arai, all of Palo Alto, Calif.

[73] Assignee: DNAX Research Institute of Molecular and Cellular Biology, Inc., Palo Alto, Calif.

[21] Appl. No.: 942,600

[22] Filed: Dec. 17, 1986

Related U.S. Application Data

[62] Division of Ser. No. 658,183, Oct. 5, 1984.

[51] Int. Cl.[4] .................. C12P 21/00; C12N 15/00; C12N 1/20; C07H 21/04
[52] U.S. Cl. .................. 435/68; 435/172.3; 435/320; 435/252.33; 530/351; 536/27
[58] Field of Search .............. 435/68, 172.3, 320, 435/253; 536/27

[56] References Cited

FOREIGN PATENT DOCUMENTS 091539 10/1983 European Pat. Off. .

OTHER PUBLICATIONS

Brake et al., Proc. Natl. Acad. Sci., vol. 81, pp. 4642–4646, 1984.
Taniguchi et al., Nature, vol. 302, pp. 305–310 (1983).
Parnes et al., Proc. Natl. Acad. Sci., vol. 78, pp. 2253–2257 (1981).
Maniatis et al., Molecular Cloning: A Laboratory Manual, pp. 224–228.
Brandis et al., Genetic Engineering, vol. 8, pp. 299–314 (1986).
P-L Biochemicals, The Molecular Biology Catalog, (1983).
Bleackley et al., J. Immunol., vol. 127, pp 2432–2435 (1981).
Paetkau et al., Meth. Enzymol., vol. 116, pp. 526–539 (1985).
Riendeau et al., J. Biol. Chem., vol. 258, pp. 12114–12117 (1983).
Watson et al., J. Exp. Med., vol. 150, pp. 849–861 (1979).
Mochizuki et al., J. Immunol. Meth., vol. 39, pp. 185–201 (1980).
Maeda et al., Biochem. Biophys. Res. Comm., vol. 115, pp. 1040–1047 (1983).
Devos et al., Nucleic Acids Res., vol. 11, pp. 4307–4323 (1983).

Primary Examiner—Blondel Hazel
Attorney, Agent, or Firm—William Smith; Stephen Macevicz

[57] ABSTRACT

Plasmid vectors are provided that carry complementary DNA (cDNA) clones coding for polypeptides exhibiting murine interleukin-2 activity. One of these polypeptides is 168 amino acids in length, including a potential leader sequence of about 19 amino acids. The cDNA is derived from messenger RNA isolated from a mouse T-cell line after activation with concanavalin A. The cDNA was cloned by incorporation into a plasmid vector, which is then transformed into E. coli. The plasmid vector also contained DNA segments from the SV40 virus, permitting expression of the cDNA after transfection into a mammalian host cell, such as monkey COS-7 cells.

16 Claims, 4 Drawing Sheets

FIG. 1

```
          10         20         30         40                         63
TATCACCCTT GCTAATCACT CCTCACAGTG ACCTCAAGTC CTGCAGGC ATG TAC AGC ATG CAG CTC TGT
                                                    MET Tyr Ser MET Gln Leu Ala Ser Cys
  78                                      93                108                      138
GTC ACA TTG ACA CTT GTG CTC CTT GTC AAC AGC GCA CCC ACT TCA AGC TCC ACT TCA AGC TCT ACA
Val Thr Leu Thr Leu Val Leu Leu Val Asn Ser Ala Pro Thr Ser Ser Ser Thr Ser Ser Ser Thr
  153                                                    183                        198
GCG GAA GCA CAG CAG CAG CAG CAG CAG CAG CCC ACT TCA AGC CAG CAC CTG GAG CAG TTG ATG
Ala Glu Ala Gln Gln Gln Gln Gln Gln Gln                 Gln Gln His Leu Glu Gln Leu Leu MET
  213                                228                                        258      273
GAC CTA CAG GAG CTC CTG AGC AGG ATG AGC CTA CAG GAG AAT TAC AGG AAC CTC CCC AGG ATG CTC ACC
Asp Leu Gln Glu Leu Leu Ser Arg MET Glu Asn Tyr Arg Asn Leu Lys Leu Pro Arg MET Leu Thr
              288                            303                                  318         333
TTC AAA TTT TAC TTG CCC AAG CAG GCC ACA GAA TTG GAT CTT CAG TGC CTA GAA GAT GAA CTT
Phe Lys Phe Tyr Leu Pro Lys Gln Ala Thr Glu Leu Asp Leu Gln Cys Leu Glu Asp Gln Leu
          348                          363                        378                  393
GGA CCT CTG CAT GTT CTG GAT CTG ACT CAA AGC AAA AGC TTT CAA TTG GAA GAT GCT GAG AAT
Gly Pro Leu His Val Leu Asp Leu Thr Gln Ser Lys Ser Phe Gln Leu Glu Asp Ala Glu Asn
  408                            423                        438                      453       468
TTC ATC AGC AAT ATC AGA GTA ACT GTT AAG CTA AAG CTA AAA ACA TTT GAG TGC CAA
Phe Ile Ser Asn Ile Arg Val Thr Val Lys Leu Lys Leu Lys Thr Phe Glu Cys Gln
      483                          498                                  513                528
TTC GAT GAT GAG TCA GCA ACT GAG CTG GTG GAC TTT CTG AGA ATA GCC TTC TGT CAA AGC ATC
Phe Asp Asp Glu Ser Ala Thr Glu Leu Val Asp Phe Leu Arg Ile Ala Phe Cys Gln Ser Ile
          543                              570    580                590              610
ATC TCA ACA AGC CCT CAA TAACT ATGTACCTCC TGCTTACAAC ACATAAGGCT CTCTATTTAT TTAAATATTT
Ile Ser Thr Ser Pro Gln
       620          630         640        650          660         670         680
AACTTAATT TATTTTTGGA TGTATTGTTT ACTATCTTTT GTAACTACTA GTCTTCAGAT GATAAATATG
       690         700         710         720         730        740        750
GATCTTTAAA GATTCTTTTT GTAAGCCCCA AGGGCTCAAA AATGTTTTAA ACTATTTATC TGAAATTATT
       760         770         780         790         800         810        820
TATTATATTG AATTGTTAAA TATCATGTGT AGGTAGACTC ATTAATAAAA GTATTTAGAT GATTCAAATA
TAAAA
```

CDNA CLONES CODING FOR POLYPEPTIDES EXHIBITING MURINE INTERLEUKIN-2 ACTIVITY

This is a division, of application Ser. No. 658,183 filed Oct. 5, 1984.

FIELD OF THE INVENTION

This invention relates generally to the application of recombinant DNA technology to elucidate the control mechanisms of the mammalian immune response and, more particularly, to the isolation of deoxyribonucleic acid (DNA) clones coding for polypeptides exhibiting murine interleukin-2 activity.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

This technology has progressed extremely rapidly in recent years, and a variety of exogenous proteins have been expressed in a variety of hosts. By way of example, some of the eukaryotic proteins so-produced include: proinsulin (Naber, S. et al., Gene 21: 95–104 [1983]); interferons (Simon, L. et al., Proc. Nat. Acad. Sci. U.S.A., 80: 2059–2062 [1983] and Derynck, R. et al., Nucl. Acids Res. 1: 1819–1837 [1983]); growth hormone (Goeddel, D., et al., Nature 281: 544–548 [1979]) and mast cell growth factor (Yokota et al., Proc. Nat. Acad. Sci. U.S.A., 81: 1070–1074 [1984]. (These publications and other reference materials have been included to provide additional details on the background of the pertinent art and, in particular instances, the practice of invention, and are all incorporated herein by reference.)

For some time, it has been dogma that the mammalian immune response was due primarily to a series of complex cellular interactions, called the "immune network". While it remains clear that much of the response does in fact revolve around the network-like interactions of lymphocytes, macrophages, granulocytes and other cells, immunologists now generally hold the opinion that soluble proteins (e.g., the so-called lymphokines) play a critical role in controlling these cellular interactions.

Lymphokines apparently mediate cellular activities in a variety of ways. They have been shown to have the ability to support the proliferation and growth of various lymphocytes and, indeed, are thought to play a crucial role in the basic differentiation of pluripotential hematopoietic stem cells into the vast number of progenitors of the diverse cellular lineages responsible for the immune response. Cell lineages important in this response include two classes of lymphocytes: B cells, which can produce and secrete immunoglobulins (proteins with the capability of recognizing and binding to foreign matter to effect its removal), and T cells (of various subsets) that induce or suppress B cells and some of the other cells (including other T cells) making up the immune network.

Research to better understand (and thus potentially treat therapeutically) immune disorders, through the study of B cells, T cells and the other cells involved in the immune response, has been hampered by the general inability to maintain these cells in vitro. However, several immunologists recently discovered that such cells could be isolated and cultured by growing them on secretions from other cells, e.g., conditioned media from splenic lymphocytes stimulated with Concanavalin A (ConA). It has now become clear from this work that the generation of cell clones is dependent on specific factors, such as lymphokines.

Some of the better characterized lymphokines are the so-called interleukins, e.g., lymphocyte activating factor (LAF), which is released from macrophages and can induce replication of thymocytes and peripheral T cells (Mizel, S. et al., J. Immunol. 120: 1497–1503 [1978]), T cell growth factor (TCGF), which was initially detected in conditioned media from lectin-stimulated lymphocytes (Morgan, D. et al., Science 193: 1007–1008 [1976]), and mast cell growth factor (MCGF), which was found in lectin-stimulated T cell clones (Nabel, G. et al., Nature 291: 332–334 [1981]). In 1979, the Second International Lymphokine Workshop labelled LAF as interleukin-1 (IL-1) and TCGF, as interleukin-2 (IL-2). Similarly, although not officially, MCGF is now known generally as interleukin-3 (IL-3) (Ihle, J. et al., J. Immunol. 131: 282–287 [1983]).

In view of the central role T cells play in the immune response, their growth factor, IL-2, has been the subject of considerable study since its discovery about 10 years ago (Smith, K. Immunol. Rev. 51: 337–357 [1980]). IL-2's prime function is almost certainly the stimulation and maintenance of proliferation of most T cell subsets. In fact, the removal of IL-2 from proliferating T cells results in their death within a few hours (Ruscette, F. et al., J. Immunol. 123: 2928–2931 [1977]). IL-2 has also been shown to be one of the lymphokines responsible for cytotoxic T lymphocyte generation, as well as differentiation and induction of function.

Importantly, IL-2's function is not restricted to being just a growth factor for activated T cells. The secretion by T cells of γ-interferon and B cell growth factors appears to be induced by IL-2 (Torres, B. et al., J. Immunol, 126: 1120–1134 [1982] and Howard, M. et al., J. Exp. Med. 158: 2024–2039 [1983]). Indeed IL-2 may be at the center of the lymphokine mediated immune response (for a detailed description of IL-2 activities, see Farrar, J. et al., Immunol. Rev. 63: 129–166 [1982].

Several procedures have been developed for the isolation and purification of IL-2 (e.g., Watson, J. et al., J. Exp. Med. 150: 849–855 [1979]; Engleman, E. et al., J. Immunol. 127: 2124–2127 [1981]; and U.S. Pat. Nos. 4,404,280 and 4,407,945). These procedures generally entail culturing normal spleen cells or certain lymphoma cell lines, and then stimulating the cells with a mitogen. This often results in relatively low concentrations of IL-2 in the cell media, which makes subsequent concentration and purification a formidable task.

Furthermore, the IL-2 preparations almost undoubtedly contain some residual mitogen, as well as contaminating proteins from the IL-2 producing cell line. The development of murine T cell hybridomas producing IL-2 has mitigated the mitogen contamination, but the problem remains that most, if not all, murine IL-2 preparations contain other immunological proteins. These proteins can influence assay results, and thus interfere with the unequivocable determination of the precise range of IL-2 activities.

In the human system, these problems have been basically alleviated by the successful cloning and expression of cDNA's encoding for human IL-2 (Taniguchi, T. et al., Nature 302: 305–310 [1983] and Devos, R. et al., Nucl. Acids Res. 11: 4307–4323 [1983]), but the problems remain in the murine system. Given that most immunological experiments are still performed on mice or mouse-derived cells, research is still greatly hampered.

Indeed, the molecular properties of IL-2 remain uncertain. Although it presently appears that the molecular weight of IL-2 is approximately 30–35,000 daltons (Shaw, J. et al., J. Immunol. 120: 1967–1973 [1978]), at least one investigator believes that murine IL-2 is a dimer made up of two 16,000 dalton components (Caplan, B. et al., J. Immunol, 126: 1351–1354 [1981]). Translation in *Xenopus laevis* oocytes of size fractionated mRNA (indicating that one or more murine mRNA species of about 1000 to 1100 nucleotides encode a protein exhibiting IL-2 activity) has shed some light on the question (Bleackley, R. et al., J. Immunol. 127: 2432–2435 [1981]), but research has still been slowed by the absence of coding sequences and means for producing large quantities of the desired protein.

Clarification of many of the outstanding issues relating to the molecular biology of murine interleukin-2 requires additional structural data, e.g., substantially full-length sequence analysis of the protein and nucleic acid molecules in question. Protein sequencing offers, of course, a possible means to resolve the matter to a certain degree, but it is very difficult work experimentally and often can provide neither completely accurate nor full-length amino acid sequences. In fact, murine IL-2 appears to be blocked near the $NH_2$ terminus, rendering protein sequencing even more difficult.

Moreover, having the capability of making bulk quantities of a polypeptide exhibiting murine IL-2 activity (and substantially free from other murine proteins) will greatly facilitate the study of the biology of T cells and other cells involved in the immune response; e.g., by minimizing the necessity of relying on lectin-conditioned media for stimulating cell growth. Accurate and complete sequence data on murine IL-2 will help elucidate the structure of that compound and also serve to simplify the search for other immunological factors. Finally, additional information on any lymphokine will help in evaluating the roles of the various growth factors and cells of the immune network and thus provide insight into the entire immune system -with the concomitant therapeutic benefits.

Thus, there exists a significant need for extensive nucleotide sequence data on the DNAs coding for, and amino acid sequences of, proteins exhibiting murine IL-2 activity, as well as a simple and economic method of making substantial and essentially pure quantities of such materials. The present invention fulfills these needs.

SUMMARY OF THE INVENTION

The present invention provides cDNA clones coding for polypeptides exhibiting murine IL-2 activity. A nucleotide sequence for a cDNA and a putative amino acid sequence for an associated polypeptide are shown in FIG. 1. The cDNA sequence can be integrated into various vectors, which in turn can direct the synthesis of the corresponding polypeptides in a variety of hosts, including eukaryotic cells, such as mammalian cells in culture.

More specifically, the invention provides a process for producing a polypeptide exhibiting murine interleukin-2 activity, the process comprising the steps of:
(a) providing a vector comprising a nucleotide sequence coding for the polypeptide, wherein the nucleotide sequence is capable of being expressed by a host containing the vector;
(b) incorporating the vector into the host; and
(c) maintaining the host containing the vector under conditions suitable for expression of the nucleotide sequence into the polypeptide.

Preferably, the cDNA sequences are derived from an mRNA sequence coding for the polypeptides, and the host is an organism such as a eukaryotic, e.g. mammalian, cell transfected or transformed with the vector. Further, the vector preferably comprises also a second nucleotide sequence capable of controlling expression of the nucleotide sequence coding for the polypeptide. This second sequence coding can include a promoter sequence, one or more intron sequences and a polyadenylation sequence, to permit, respectively, transcription, splicing and polyadenylation of the nucleotide sequence coding for the polypeptide. Particularly, when the host is a mammalian cell, such as a COS-7 (monkey kidney) cell, the vector contains the promoter sequence of the simian virus 40 (SV40) early region promoter and the polyadenylation sequence of the SV40 late region polyadenylation sequence.

The mouse cDNA sequence of FIG. 1 (see below), or a portion thereof, is capable of hybridizing with other DNA sequences, such as DNA coding for other mammalian growth factors from a cDNA or genomic library. It is noted that the described cDNA sequences seem to contain information for a leader sequence.

The polypeptides of the present invention are capable of enhancing growth of murine T cell and other cells, particularly in cultures in vitro. Suitable compositions for sustaining IL-2 receptive cell lines can be prepared by adding the polypeptides (preparations of which are essentially free of other murine growth factors) to well known cell growth media formuations.

Other features and advantages of the invention will become apparent from the following detailed description, which describes, in conjunction with the accompanying drawings and by way of example, the present invention.

BRIEF DESCRIPTION OF THE FIGURES

FIG. 1 illustrates the nucleotide sequence and putative corresponding amino acid sequence of a cDNA clone exhibiting murine IL-2 activity;

DESCRIPTION OF THE SPECIFIC EMBODIMENTS

In accordance with the present invention, cDNA clones are provided that code for polypeptides exhibiting IL-2 activity. After the cDNA sequences have been incorporated into replicable expression vectors, and the vectors transfected into an appropriate host (e.g. a mammalian cell culture), the expressed polypeptide or polypeptides have the ability to allow the expansion of T cells and their related lineages.

An exemplary, putative amino acid sequence based on the isolated nucleotide sequence is shown in FIG. 1. The murine IL-2 cDNA contains a single open-reading frame consisting of 168 codons. Downstream of the putative initiation codon is a region rich in hydrophobic amino acids. Including the asparagine codon at amino acid position 19, there is a stretch of nine continuous amino acids identical to that predicted for human IL-2. The alamine residue in this sequence coincides with the $NH_2$-terminal amino acid deduced for human IL-2 (Stern, A. et al., Proc. Nat. Acad. Sci. U.S.A. 81: 871–875[1984]). It is likely, therefore, that the mature form of secreted mouse IL-2 begins with an alanine residue, and the preceeding 20 amino acids constitute a leader region, which is subject to removal by proteolytic processing. Thus, mature murine IL-2 would consist of about 149 amino acids, with a calculated molecular weight of approximately 16,000 daltons (unglycosylated). The mature protein probably contains 20 acidic (Asp+Glu) and 14 basic (Arg+Lys) amino acids, the difference in numbers perhaps accounting for the acidic isolectric point (pI=4.3–4.9) of the protein (Watson, J. et al., J. Exp. Med. 150: 849–861 [1979]). There do not appear to be any potential N-glycosylation sites (Asn-X-Ser/Thr) (Neuberger, A. et al., Glycoproteins 5, 450–490, Elsevier Publishing Co., U.S.A. [1972]), however, the presence of other in vivo modifications, such as sialylation or o-glycosylation, cannot be excluded.

When transfected into COS-7 monkey cells or other suitable expression systems, cDNA clones of this invention can direct the synthesis of biologically active murine IL-2. Addition of this expressed cloned gene product to cultures of mouse T cells allows expansion of receptive cells and/or their maintenance in culture. The expressed polypeptides can exhibit the assorted activities associated with murine IL-2.

A variety of methods may be used to prepare the cDNAs of the present invention. By way of example, total mRNA is extracted (e.g., as reported by Berger, S. et al., Biochemistry 18: 5143–5149 [1979]) from cells (e.g. a hybrid cell line) producing polypeptides exhibiting murine IL-2 activity. The double-stranded cDNAs from this total mRNA can be constructed by using primer-initiated reverse transcription (Verma, I., Biochim. Biophys. Acta, 473: 1–38 [1977]) to make first the complement of each mRNA sequence, and then by priming for second strand synthesis (Land, H. et al., Nucleic Acids Res., 9: 2251–2266 [1981]). Subsequently, the cDNAs can be cloned by joining them to suitable plasmid or bacteriophage vectors (Rougeon, F. et al., Nucleic Acids Res., 2, 2365–2378 [1975] or Scherer, G. et al., Dev. Biol. 86, 438–447 [1981]) through complementary homopolymeric tails (Efstratiadis, A. et al., Cell, 10, 571–585 [1977]) or cohesive ends created with linker segments containing appropriate restriction sits (Seeburg, P. et al., Nature, 270, 486–494 [1977] or Shine, J. et al., Nature, 270, 494–499 [1977]), and then transforming a suitable host. (See generally Efstratiadis, A., and Villa-Kormaroff, L., "Cloning of double stranded cDNA" in Setlow, J. and Hollaender, A. (eds.) Genetic Engineering, Vol. 1, L Plenum Publishing Corp., N.Y., U.S.A. [1982].)

A preferred method of obtaining the full-length cloned cDNAs of this invention is the procedure developed by H. Okayama and P. Berg (Mol. and Cell. Biol., 2: 161–170 [1982]). This method has the advantage of placing the cDNA inserts in a bacterial cloning vector at a position whereby the cDNA can also be directly translated and processed in mammalian cells. Briefly, the first cDNA strand is primed by polydeoxythymidylic acid covalently joined to one end of a linear plasmid vector DNA. The plasmid vector is then cyclized with a linker DNA segment that bridges one end of the plasmid to the 5' end of the cDNA coding sequence. By employing a DNA fragment containing the Simian Virus 40 (SV40) early region promoter and a linker containing a modified SV40 late region intron, the cDNA can be expressed in vitro in COS-7 mouse (kidney) cells without further modification. (See generally Okayama, H. and Berg, P., Mol. and Cell. Biol., 3: 280–289 [1983] and Jolly, D. et al., Proc. Nat. Acad. Sci. U.S.A., 80: 477–481 [1983].)

Once the cDNA library in the Okayama/Berg plasmid vector has been completed, the cDNA clones are collected, and random pools are checked for the presence of the desired cDNAs by hybrid selection, translation, and assay (e.g. by measuring murine IL-2 activity, the existence of antigenic determinants, or other biological activities). Pools positive by these criteria can then be probed with an appropriate subtracted probe, e.g., cDNA from a B cell line and/or uninduced T cell line. Thereafter, the positive, probed pools are divided into individual clones which are tested by transfection into a suitable host (such as a mammalian cell culture), and the host supernatant assayed for the desired activity (e.g. TCGF activity). Positive clones are then sequenced.

The desired cDNA clones can be detected and isolated by hybridization screening with appropriate mRNA samples (Heindell, H. et al., Cell, 15: 43–54 [1978]). Alternatively, the cDNA libraries can be screened by hybrid selection (Harpold, M. et al., Nucleic Acid Res., 5: 2039–2053 [1978] or Parnes, J. et al., Proc. Nat. Acad. Sci. U.S.A., 78: 2253–2257 [1981]) or in Xenopus oocytes (Aurdon, J., Nature, 233: 177–182 [1971]). (See generally Villa-Komaroff, L. et al., Proc. Nat. Acad. Sci. U.S.A. 75: 3727–3731 [1978].)

In further describing the procedures relating to preparing cDNA clones of the invention, the assay cell line and other lines will be considered first, followed by general descriptions of the procedures for isolating mRNA coding for a protein exhibiting murine IL-2 activity; the construction of a cDNA library containing the cDNA sequences; isolation of full-length cDNA clones in a plasmid vector and subsequent expression in mammalian cells; subcloning and expression in bacteria and yeast; and purification and formulation. A more detailed description of the entire experimental process will follow thereafter.

T Cell and Other Lines

Any of a large variety of different cells may be used as sources for murine IL-2 activity and in the assay thereof (see, e.g., Robert-Guroff, M. et al., "T-Cell Growth Factor"; *Growth and Maturation Factors*, ed.

Guroff, G., New York: John Wiley and Sons, pgs. 267–308 at 287 [1984] and U.S. Pat. Nos. 4,404,280 and 4,407,945). A preferred source is LB2-1 (ATCC accession number CRL-8629), but the mouse T lymphoma EL-4 (Farrar, J. et al., J. Immunol. 125: 2555–2558 [1980]) or other cells producing IL-2 activity are acceptable. The LB2-1 cell line was derived from a C57BL/6 mouse immunized with chicken red blood cells (CRBC) of the MHC genotype $B^2/B^2$. This line can be stimulated by $B^2/B^2$ CRBC in the presence of syngeneic spleen cells, by allogeneic spleen cells bearing the a or d m/s haplotype, or by ConA. LB2-1 can be grown on alternating cycles of antigen plus spleen stimulator cells followed by several days of IL-2 dependent proliferation (see, Clayberger, C. et al., J. Exp. Med. 157: 1906–1919 [1983]).

Similarly, a preferred cell line for use in connection with murine IL-2 activity assays is the HT-2 line and those developed as described by Watson, J. (J. Exp. Med. 157: 1906–1919 [1983]). Mouse thymocytes (Disabato, G. et al., Cell. Immunol. 17: 494–504 [1975]) cloned cytotoxic T cell lines (Morgan, D. et al., Science 193: 1007–1008 [1976]), and other murine IL-2 responsive lines are also suitable. The HT-2 line may be grown in complete medium, which includes RPMI 1640, 10% fetal bovine serum, 0.05 mM 2-mercaptoethanol and partially purified spleen cell supernatant.

To determine IL-2 activity using the HT-2 cells, a colorimetric proliferation assay is preferably utilized (Mosmann, T., J. Immunol. Methods 65: 55–63 [1983]). However, the microassay procedure of Gillis, S. et al. (J. of Immunol. 120: 2027–2032 [1978]), indirect assays (e.g., Granelli-Pipeno, A. et al., J. Exp. Med. 154: 422–430 [1981]), or other well known assay systems are suitable. Units of TCGF can be calculated by determining the dilution of factor required to give 50% of the maximum stimulation, with one unit defined as the amount of IL-2 required to give 50% of the maximum signal using 2,000 HT-2 cells in a volume of 0.01 ml.

Isolation of mRNA and Construction of a cDNA Library

Total cellular mRNA can be isolated by a variety of well-known methods (e.g., Przybla. A. et al., J. Biol. Chem. 254: 2154–2158 [1979]), but the preferred is the granidinium-thiocyanate extraction procedure of Chirgwin et al. (Biochemistry, 18: 5294–5299 [1979]). If this method is used, approximately 10 μg of polyA+ mRNA, selected on columns of oligo (dT) cellulose, is obtained from $1-2\times 10^8$ activated T cells, such as LB2-1.

The cDNA library from the polyA+ mRNA can best be constructed using the pcDV1 vector-primer and the pL1 linker fragment [available from P-L Biochemicals Inc., Milwaukee, WI) according to procedures which result in greatly enriched full-length copies of mRNA transcripts (e.g. Okayama, H. and Berg. P., Mol. Cell Biol., 2, 161–170 [1982] and Mol. Cell Biol., 3, 280–289 [1983]). The plasmid vector, which contains SV40 early promoter and SV40 RNA processing signals, is designed to promote expression of the cloned cDNA segment in mammalian cells.

Using the Okayama and Berg procedure, the cyclized vector-cDNA preparation is transformed into a competent bacterial cell, such as E. coli MC1061 cells (Casadaban, M. and Cohen, S., J. Mol. Biol., 138: 179–207 [1980]) using calcium chloride (Cohen, S. et al., Proc. Nat. Acad. Sci. U.S.A., 69: 2110–2114 [1972]). Starting with 5 μg of polyA+ RNA from ConA-stimulated Cl~Ly 1+2−/9 cells, about $1.5\times 10^6$ independent transformants are obtained. About $10^4$ clones are picked up individually and inoculated into wells of microtiter plates (Flow Laboratories Inc., McLean, Va.) containing 200 μl of L-broth, 50 μg/ml of ampicillin, and 7% DMSO. If desired, sublibraries based on the size of cDNA insert are prepared from total cDNA library as described by Okayama, H. and Berg, P. (Mol. Cell Biol., 3, 280–289 [1983]). Briefly, plasmid DNA is digested with SalI, ClaI, and HindIII separately, and electrophoresed in 1% agarose gel. After staining with ethidium bromide, the gel is sliced into 7 sections corresponding to cDNA insert sizes of 0 to 1, 1 to 2, 2 to 3, 3 to 4, 4 to 5, 5 to 6, and more than 6 kilobases (kb). DNA is extracted from each slice, recyclized with T4 DNA ligase, and used to transform MC1061. All nucleotide sequencing can be performed according to the procedure of Maxam, A. and Gilbert, W. (Methods Enzymol., 65: 499–560 [1980]).

DNA Transfections Into Monkey Cells

Approximately $1\times 10^6$ COS-7 monkey kidney cells are seeded onto 60 mm plates the day prior to transfection. Transfections are best performed with 15 μg of plasmid DNA in 1.5 ml of DME containing 50 mM Tris.HCl, pH 7.4, and 400 μg/ml DEAE-Dextran (Pharmacia Fine Chemicals, Uppsala, Sweden). This solution is then removed after 4 hr and replaced with 2.0 ml DME+4% fetal calf serum. The medium is collected after 72 hr and assayed for murine IL-2 activity as described above. DNA transfections may be carried out in L-cells and a variety of other cell sources as well (see below).

Expression in E. coli, in Yeast and in Cell Culture

Prokaryotes, such as E. coli, are very suitable for expression of the polypeptides of the present invention (see, for example, U.S. Pat. Nos. 4,338,397 and 4,411,994), provided glycosylation is not desired. To obtain high expression levels, promoters should be utilized, such as the β-lactamase (penicillinase) and lactose promoter systems (Change et al., Nature, 275: 615 [1978]; Itakura et al., Science, 198: 1056 [1977]; Goeddel et al., Nature 281: 544 [1979] or a tryptophan (trp) promoter system (Goeddel et al., Nucleic Acids Res., 8: 4057 [1980]) in conjunction with Shine-Delgarno sequences.

Those skilled in the art will realize that not only prokaryotes but also eukaryotic microbes, such as yeast, may also be used in protein production. Saccharomyces cerevisiae is a preferred eukaryotic microorganism. Suitable promoting sequences in yeast vectors include the promoters for 3-phosphoglycerate kinase (Hitzeman et al., J. Biol. Chem., 255: 12073–12080 [1980]) or other glycolytic enzymes (Hess et al., Adv. Enzyme Reg., 7: 149–167 [1969]; Holland et al., Biochemistry, 17: 4900–4907 [1978]). Other promoters that have the additional advantage of transcription controlled by growth conditions may be used. Basically any plasmid vector containing a yeast-compatible promoter, an origin of replication and termination sequences is suitable.

Figure 4A:
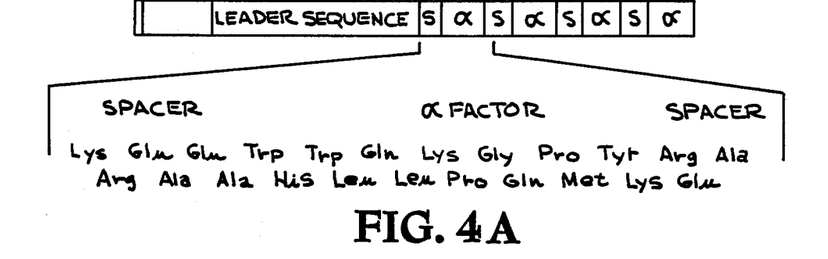
FIG. 4A shows the structure of yeast prepro-alpha-factor, including the amino acid sequence of the first spacer alpha-factor and a portion of the second spacer.

The preferred method of making murine IL-2 employing the cDNA's of the present invention itilizes the yeast mating pheromone α-factor secretory pathways (Julius, D. et. al., Cell S. cerevisiae secretes mating-type specific olibopeptide pheromones. MATα cells secrete α-factor, which induces the growth arrest of MATa cells at G1 phase of the cell cycle (Thorner, J., "The Molecular Biology of the Yeast Saccharomyces", Cold Spring Harbor Laboratory, NY [1981]; see particularly pages 143-180). The α-factor is initially synthesized as a larger precursor molecule consisting of an NH₂-terminal signal sequence of about 20 amino acids, followed by an additional 60 amino acids leader sequence and ending with four identical tandem repeats of the mature α-factor sequence. The repeats are separated from each other by six or eight amino acids spacers (Lys-Arg-Glu-Ala-Glu-Ala and Lys-Arg-Glu-Ala-Glu-[or Asp-]-Ala-Glu-Ala). This prepro-α-factor is cleaved at several specific sites. The first processing is the cleavage of the COOH-terminal side of the Lys-Arg pair of the spacer sequence catalysed by the KEX2 product (Julius et al., Cell 37: 1075-1089 [1984]). Carboxypeptidase-B like enzyme cleaves at the NH₂-terminal side of the Lys-Arg pair. The final step is the removal of Glu-Ala or Asp-Ala pairs by diaminopeptidase, which is encoded by the STE13 (See FIG. 4A). Brake, J. et al. (Proc. Nat. Acad. Sci, U.S.A. 81: 4642-4646 [1984]) have shown that the fusion of the sequence encoding mature human proteins (including human IL-2) to the first processing site allowed secretion of such proteins.

Figure 4B:
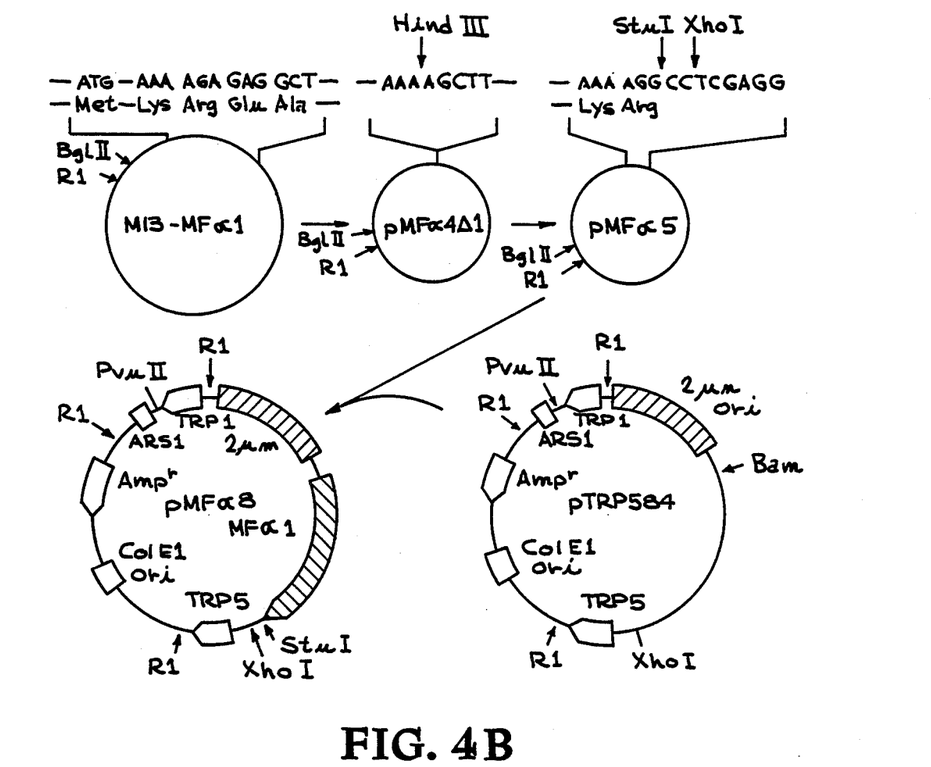
FIG. 4B shows the construction of a general yeast construction vector, designated pMFα8.

A general yeast expression vector, designated pMF-alpha-8, containing the alpha factor promoter and downstream leader sequence in conjunction with other elements, has been deposited with the ATCC (accession number 40140). It can be constructed as follows (See FIG. 4B).

A 1.7 kb EcoRI fragment carrying the MFα1 gene (Kurjan, J. and Hershowitz, I., Cell. 30: 933-943 [1982]) is cloned into the EcoRI restriction site of M13mp8 (Viera, J. and Messing, J., Gene 19: 259-268 [1982]). In order to introduce a HindIII site after the lysine codon of the first spacer region, the synthetic oligonucleotide TCTTTTATCCAAAGATACCC is hybridized to the single strand M13-MFα1 DNA and the oligonucleotide primer extended by DNA polymerase I Klenow fragment. After S1 nuclease treatment, the DNA is cleaved with EcoRI and the fragment carrying the MFα1 promoter and leader sequence cloned into the EcoRI and filled-in HindIII restriction sites of pUC8 (Viera, J. and Messing, J. above). One plasmid with the desired structure can be isolated (designated pMFα4Δ1 in FIG. 4B). The pMFα4Δ1 is cleaved with HindIII and partially filled in with DNA polymerase I Klenow fragment in the presence of dATP and dGTP. The DNA is treated with mung bean nuclease, and the oligonucleotide linker GCCTCGAGGC attached. The resultant plasmid (designated pMFα5 in FIG. 4B) will have a StuI cleavage site immediately after the arginine codon, followed by the XhoI restriction site. An S. cerevisiae-E. coli shuttle vector (pTRP584) can be constructed as follows: the PstI-XbaI fragment carrying 2 μm plasmid replication origin (Broach, J. above) is cloned into the ClaI restruction site of pTRP56 (Miyajima et al., Mol. Cell. Biol. 4: 407-414 [1984]) and the StuI restriction site within the TRP1-ARS1 fragment converted to PvuII restriction site by PvuII linker insertion. The KpnI restriction site in the original pTRP56 is converted to XhoI by the XhoI linker insertion. The general secretion vector pMFα8 is then obtained by insertion of the BglII-XhoI fragment of pMFα5 into the BamH1-XhoI restriction sites of pTRP584.

Those silled in the art will realize that cDNA clones encoding for murine IL-2 may then be readily inserted into the pMFα8 vector and subsequently transformed in yeast for IL-2 production. By way of example, the PstI-BamH1 fragment carrying the entire IL-2 cDNA is transferred from pcD-IL-2 into the PstI-BamH1 sites of pUC9 (Viera, J. and Messing, J. above) and cleaved with HinP1 and SmaI. SmaI cleaves downstream of the cDNA insert. The fragment is treated with DNA polymerase I Klenow fragment in the presence of dCTP and treated with mung bean nuclease. The frament is then cloned into the StuI restriction site of pMFα8. This plasmid DNA (carrying the TRP1 gene) can be introduced into yeast cells by the lithium acetate method (Ito, H. et al., J. Bacteriol. 153: 163-168 [1983]) and transformants selected in synthetic medium lacking tryptophan. Transformants are then grown in a common medium supplemented with 0.5% casamino acids. For harvesting, the yeast cells, resuspended in phosphate-buffered-saline (PBS) containing 1 mM PMSF, are disintegrated by vigorous shaking with acid washed glass beads. Clear supernatant is obtained by centrifugation at 10,000 rpm for 15 min.

In addition to microorganisms, cell cultures derived from multicellular organisms (especially mammalian cells) may also be used as hosts. Examples of such useful host cell lines are HeLa cells, Chinese hamster ovary cell lines, and baby hamster kidney cell lines. Expression vectors for such cells ordinarily include, as necessary, an origin of replication, a promoter located in front of the gene to be expressed, along with any required ribosome binding sites, RNA splice sites, polyadenylation sites, and transcriptional terminator sequences. When used in mammalian cells, the expression vector often has control functions provided by viral material. For example, commonly used promoters are derived from polyoma, Adenovirus 2, and most frequently SV-40. (See, e.g., U.S. Pat. No. 4,399,216 and Gheysen, D. and Fiers, W., J. of Mol. and Appl. Genetics 1: 385-394 [1982]).

Purifications and Formulations

The murine IL-2 polypeptides expressed in E. coli, in yeast or in other cells can be purified according to standard procedures of the art, including ammonium sulfate precipitation, fractionation column chromatography (e.g., ion exchange, gel filtration, electrophoresis, affinity chromatography, etc.) and ultimately crystallization (see generally "Enzyme purification and Related Techniques", Methods in Enzymology, 22: 233-577 [1977]). Once purified, partially or to homogeneity, the polypeptides of the invention may be used for research purposes, e.g., as a supplement to cell growth media (e.g., minimum essential medium Eagle, Iscove's modified Dulbecco Medium or RPMI 1640; available from Sigma Chemical Company, St. Louis, MO and GIBCO Division, Chagrin Falls, OH) and as an antigenic substance for eliciting specific immunoglobulins useful in immunoassays, immunofluorescent stainings, etc. (See generally "Immunological Methods", Vols. I & II, Eds. Lefkovits, I. and Pernis, B. Academic Press, New York, N.Y. [1979 and 1981]; and "Handbook of Experimental Immunology", ed. Weir, D., Blackwell Scientific Publications, St. Louis, MO [1978].)

If yeast cultures containing cDNA's of the present invention are utilized to prepare murine IL-2, purification preferably is accomplished as follows. Up to one liter of 12 hr culture fluid is diluted with an equal volume of 0.2% trifluoroacetic acid (TFA) and 40% CH₃CN, and pumped directly onto a 4.6×75 mm propyl column (Ultrapare RPSC, Altex, Berkeley, CA)

previously equilibrated with 0.1% TFA, 20% $CH_3CN$. Sample application can be at a flow rate of about 1 ml/min at 4° C. When all the sample has been applied, the column is connected to a conventional HPLC system at room temperature, and further washed at 0.5 ml/min until the absorbance monitored at 214 nM reaches baseline. A gradient of increasing solvent concentration is then applied (0.5% $CH_3CN$ per min), and 1 ml fractions collected. The murine IL-2 elutes about 65 min after the start of the gradient in a peak well separated from other proteins. Analysis of the peak fractions on silver-stained Laemmli gels (Laemmli, U., Nature 227: 680–685 [1970]) should indicate that the protein is >95% pure.

The following experimental information and data are offered by way of example and not by way of limitation.

EXPERIMENTAL

A. Cloned LB2-1 T Cells (1) A clone of T Cells LB2-1 (ATCC accession number CRL-8629) expressing the Thy 1+ Ly 1+2−phenotype is continuously maintained at $0.5 \times 10^5$ cells/ml in RPMI-1640 with 10% heat-inactivated fetal calf serum, $5 \times 10^{-5}$M 2-ME, 2 mM glutamine, non-essential amino acids, and essential vitamins conditioned with 5% DEAE treated supernatants from ConA treated Lewis strain rat spleen cells.

(2) ConA-activation of LB2-1 cells: The cells are cultured at $5 \times 10^5$/ml in DME with 4% heat-inactivated fetal calf serum, $5 \times 10^{-5}$M 2-ME, 2 mM glutamine, non-essential amino acids, essential vitamins and 4 μg/ml ConA. After 12–14 hrs.' incubation at 37° C. in 10% $CO_2$, the cell suspension is centrifuged at 1500 rpm for 10 minutes. The cell pellets are collected and frozen immediately at −70° C. The supernatants are filtered (Nalgene-0.22 microns) and stored at −80° C. as a source of growth factors. Aliquots of the supernatant are assayed for murine IL-2 activity (see below) to verify the induction of the line by the ConA treatment.

B. Cloned HT-2 Cells

The T cell line utilized in the murine IL-2 assays was HT-2, a line first described by Watson, J. (J. Exp. Med. 150: 1510–1519 [1979]). It is continuously maintained with doubling times of about 24 hours in RPMI 1640 with 10% heat-inactivated FCS, $5 \times 10^{-5}$M 2-ME and 2 mM glutamine, non-essential amino acids and essential vitamins supplemented with 5% supernatant from ConA-activated LB2-1 cells. The growth of the HT-2 cell clone is dependent on the active growth factor(s) obtained from the supernatant of stimulated LB2-1 cells.

C. Tetrazolium Salt (MTT) Colorimetric Assay for Murine IL-2.

(1) About 2000 cells were cultured in flat-bottomed 96 well microtiter trays in 0.1 ml of DME supplemented with co-factors and test supernatant as described above.

(2) The trays were incubated at 37° C. in 10% $CO_2$. After twenty hours, 0.01 ml of 5 mg/ml MTT (3-(4,5-dimethylthiazol-2-yl)-2,5-diphenyl tetrazolium bromide, Sigma Chemical Co., St. Louis, MO) in phosphate-buffered saline (PBS) was added to each culture. Four hours later 0.1 ml of 0.04N HCl in isopropanol was added to each culture and thoroughly mixed. After a few minutes, the plates were read on a Dynatech MR580 Microelisa Auto Reader (Dynatech Instruments, Inc., Torrance, CA), at a wavelength of 570 nm (reference wavelength of 630 nm) and a calibration setting of 1.99.

D. Isolation of mRNA from LB2-1 Cells.

(1) Total cellular RNA was isolated from cells using the guanidine isothiocyanate procedure of Chirgwin, J. et al., (Biochemistry, 18: 5294–5299 [1979]).

Frozen cell pellets from uninduced or ConA-induced LB2-1 cells (6, 8, and 11 hr after stimulation) were suspended in guanidine isothiocyanate lysis solution. Twenty ml of lysis solution was used for $1.5 \times 10^8$ cells. Pellets were resuspended by pipetting, then DNA was sheared by 4 passes through a syringe using a 16 gauge needle. The lysate was layered on top of 20 ml of 5.7M CsCl, 10 mM EDTA in 40 ml polyallomer centrifuge tube. This solution was centrifuged at 25,000 rpm in a Beckman SW28 rotor (Beckman Instruments, Inc., Palo Alto, CA) for 40 hrs at 15° C. The guanidine isothiocyanate phase containing DNA was pipetted off from the top, down to the interface. The walls of the tube and interface were washed with 2–3 ml of guanidine isothiocyanate lysis solution. The tube was cut below the interface with scissors, and the CsCl solution was decanted. RNA pellets were washed twice with cold 70% ethanol. Pellets were then resuspended in 500 μl of 10 mM Tris.HCl pH 7.4, 1 mM EDTA, 0.05% SDS. 50 μl of 3M sodium acetate was added and RNA was precipitated with 1 ml ethanol. About 0.3 mg total RNA was collected by centrifuging and the pellets washed once with cold ethanol.

(2) PolyA+ mRNA isolation:

Washed and dried total RNA pellet was resuspended in 900 μl of oligo (dT) elution buffer (10 mM Tris.HCl, pH 7.4, 1 mM EDTA, 0.5% SDS). RNA was heated for 3 min. at 68° C. and then chilled on ice. 100 μl of 5M NaCl was added. The RNA sample was loaded onto a 1.0 ml oligo (dT) cellulose column (Type 3, Collaborative Research, Waltham, MA) equilibrated with binding buffer (10 mM Tris.HCl pH 7.4, 1 mM EDTA, 0.5M NaCl, 0.5% SDS.). Flow-through from the column was passed over the column twice more. The column was then washed with 20 ml binding buffer. PolyA+ mRNA was collected by washing with elution buffer. RNA usually eluted in the first 2 ml of elution buffer. RNA was precipitated with 0.1 volume 3M sodium acetate (pH 6) and two volumes of ethanol. The RNA pellet was collected by centrifugation, washed twice with cold ethanol, and dried. The pellet was then resuspended in water. Aliquots were diluted, and absorbance at 260 nm was determined.

E. Oocyte Injection

Oocytes were removed from female *Xenopus laevis* and incubated in Barth's solution (88 mM NaCl, 1 mM KCl, 0.33 mM $Ca(NO_3)_2$, 0.41 mM $CaCl_2$, 0.82 mM $MgSO_4$, 2.4 $NaHCO_3$, and 10 mM HEPES (pH 7.9) (Sigma Chemical Co., St. Louis, MO). Injection clusters of 2–3 oocytes were prepared. RNA samples were to be injected dissolved in injection buffer (40 mM Tris.HCl pH 7.4, 0.35M NaCl). Total polyA+ mRNA was resuspended at a concentration of 500 μg/ml in injection buffer, while RNA samples eluted from DNA filters from hybrid selections (see below) always contained 5 μg of calf liver tRNA as carrier and were resuspended in 2 μl of injection buffer. About 40 nl aliquots were injected into each oocyte using micropipets pulled by hand with tips forged using a microforge. The pipettes were calibrated with known volumes of sterile water. Approximately 10 to 20 oocytes were injected for each mRNA sample. The injected oocytes were incubated in groups of two or three in individual wells of 96-well microtiter dishes containing 10 μl of Barth's solution+1% bovine serum albumin per oocyte. The oocytes were kept at 19° C. for 48 hours. Thereafter, supernatants from triplicate pools of six oocytes each were assayed for IL-2 activity. The supernatants were first sterilized by centrifuging for 10 minutes in a microcentrifuge and then assayed. Supernatants from uninjected oocytes were always collected as a control.

The assay results from supernatants collected from untreated or ConA-stimulated LB2-1 cells are shown in Table I. Titration of all samples, including the reference standard, was performed in triplicate. Units of IL-2 were calculated by determining the dilution of factor requested to give 50% of maximum stimulation, and one unit is defined as the amount of murine IL-2 required to give 50% of the maximum signal using 2,000 HT-2 cells in a volume of 0.1 ml. LB2-1 cells were harvested at 6, 8, and 11 hr following the addition of Con A. Uninduced cells were grown identically, but omitting Con A. Poly(A)+ RNA was prepared from each cell pellet and then injected into Xenopus oocytes as described. The supernatants from stimulated and un-stimulated cells and the oocyte supernatants were assayed for TCGF activity on the HT2 cell line.

TABLE I

| Production of TCGF Activity by LB2-1 | | |
|---|---|---|
| | LB2-1 supernatant Units/$10^6$ cells | Oocyte supernatant Units/$10^6$ cell equivalents |
| without Con A | <10 | <0.5 |
| with Con A 6 hr | 10,377 | 293 |
| 8 hr | 16,496 | 52 |
| 11 hr | 14,604 | 112 |

F. cDNA Library Construction:
(1) Preparation of vector primer and oligo dG-tailed linker DNAs:
  The procedure of Okayama & Berg (Mol. & Cell. Biol. 2: 161-170 [1982]) was used with only minor modifications and adapted to the pcDV1 and pL1 plasmids described by Okayama & Berg (Mol. & Cell. Biol. 3: 380-389 [1983]).

An 80 μg sample of pcDV1 DNA was digested at 30° C. with 20 U of KpnI endonuclease in a reaction mixture of 450 μl containing 6 mM Tris.HCl (pH 7.5), 6 mM MgCl$_2$, 6 mM NaCl, 6 mM 2-ME, and 0.1 mg of bovine serum albumin (BSA) per ml. After 16 hr the digestion was terminated with 40 μl of 0.25M EDTA (pH 8.0) and 20 μl of 10% sodium dodecyl sulfate (SDS); the DNA was recovered after extraction with water-saturated 1:1 phenol-CHC13 (hereafter referred to as phenol-CHC13) and ethanol precipitation. Homopolymer tails averaging 60, but not more than 80, deoxythymidylate (dT) residues per end were added to the KpnI endonuclease-generated termini with calf thymus terminal transferase as follows: The reaction mixture (38 μl) contained sodium cacodylate-30 mM Tris.HCl pH 6.8 as buffer, with 1 mM CoCl$_2$, 0.1 mM dithiothreitol, 0.25 mM dTTP, the KpnI endonuclease-digested DNA, and 68 U of the terminal deoxynucleotidyl transferase (P-L Biochemicals, Inc., Milwaukee, WI). After 30 min. at 37° C. the reaction was stopped with 20 μl of 0.25M EDTA (pH 8.0) and 10 μl of 10% SDS, and the DNA was recovered after several extractions with phenol-CHC13 by ethanol precipitation. The DNA was then digested with 15 U of EcoRI endonuclease in 50 μl containing 10 mM Tris.HCl pH 7.4, 10 mM MgCl$_2$, 1 mM dithiothreitol, and 0.1 mg of BSA per ml for 5 hr at 37° C. The large fragment, containing the SV40 polyadenylation site and the pBR322 origin of replication and ampicillin-resistance gene, was purified by agarose (1%) gel electrophoresis and recovered from the gel by a modification of the glass powder method (Vogelstein, B. & Gillespie, D., Proc. Nat. Acad. Sci. 76: 615-619 [1979]). The dT-tailed DNA was further purified by absorption and elution from an oligo (dA)-cellulose column as follows: The DNA was dissolved in 1 ml of 10 mM Tris.HCl pH 7.3 buffer containing 1 mM EDTA and 1M NaCl, cooled at 0° C., and applied to an oligo (dA)-cellulose column (0.6 by 2.5 cm) equilibrated with the same buffer at 0° C. The column was washed with the same buffer at 0° C. and eluted with water at room temperature. The eluted DNA was precipitated with ethanol and dissolved in 10 mM Tris.HCl pH 7.3 with 1 mM EDTA.

The oligo (dG) tailed linker DNA was prepared by digesting 75 μg of pL1 DNA with 20 U of PstI endonuclease in 450 μl containing 6 mM Tris.HCl pH 7.4, 6 MgCl$_2$, 6 mM 2-ME, 50 mM NaCl, and 0.01 mg of BSA per ml. After 16 hr at 30° C. the reaction mixture was extracted with phenol-CHCl$_3$ and the DNA was precipitated with alcohol. Tails of 10 to 15 deoxyguanylate (dG) residues were then added per end with 46 U of terminal deoxynucleotidyl transferase in the same reaction mixture (38 μl) as described above, except that 0.1 mM dGTP replaced dTTP. After 20 min. at 37° C. the mixture was extracted with phenol-CHCl$_3$, and after the DNA was precipitated with ethanol it was digested with 35 U of HindIII endonuclease in 50 μl containing 20 mM Tris.HCl pH 7.4, 7 mM MgCl$_2$, 60 mM NaCl, and 0.1 mg of BSA at 37° C. for 4 hr. The small oligo (dG)-tailed linker DNA was purified by agarose gel (1.8%) electrophoresis and recovered as described above.

(2) cDNA Library Preparation:
Step 1: cDNA synthesis
The reaction mixture (10 μl) contained 50 mM Tris.HCl pH 8.3, 8 mM MgCl$_2$, 30 mM KCl, 0.3 mM dithiothreitol, 2 mM each dATP, dTTP, dGTP, and dCTP, 20 μCi $^{32}$P-dCTP (3000 Ci/mmole), 6 μg polyA+ RNA from Con-A induced LB2-1, 60 units RNasin (Biotec, Inc., Madison, WI), and 2 μg of the vector-primer DNA (15 pmol of primer end), and 45 U of reverse transcriptase. The reaction was incubated 60 min at 42° C. and then stopped by the addition of 1 μl of 0.25M ETDA (pH 8.0) and 0.5 μl of 10% SDS; 40 μl of phenol-CHCl$_3$ was added, and the solution was blended vigorously in a Vortex mixer and then centrifuged. After adding 40 μl of 4M ammonium acetate and 160 μl of ethanol to the aqueous phase, the solution was chilled with dry ice for 15 min., warmed to room temperature with gentle shaking to dissolve unreacted deoxynucleoside triphosphates that had precipitated during chilling, and centrifuged for 10 min. in an Eppendorf microfuge. The pellet was dissolved in 10 μl of 10 mM Tris.HCl pH 7.3 and 1 mM EDTA; mixed with 10 μl of 4M ammonium acetate, and reprecipitated with 40 μl of ethanol, a procedure which removes more than 99% of unreacted deoxynucleoside triphosphates. The pellet was rinsed with ethanol.

Step 2: Oligodeoxycytidylate [oligo (dC)] addition

The pellet containing the plasmid-cDNA:mRNA was dissolved in 20 μl of 140 mM sodium cacodylate-30 mM Tris.HCl pH 6.8 buffer containing 1 mM $CoCl_2$, 0.1 mM dithiothreitol, 0.2 μg of poly(A), 70 μM dCTP, 5 μCi $^{32}$P-dCTP, 3000 Ci/mmole, and 60 U of terminal deoxynucleotidyl transferase. The reaction was carried out at 37° C. for 5 min. to permit the addition of 10 to 15 residues of dCMP per end and then terminated with 2 μl of 0.25M EDTA (pH 8.0) and 1 μl of 10% SDS. After extraction with 20 μl of phenol-$CHCl_3$, the aqueous phase was mixed with 20 μl of 4M ammonium acetate, the DNA was precipitated and reprecipitated with 80 μl of ethanol, and the final pellet was rinsed with ethanol.

Step 3: HindIII endonuclease digestion

The pellet was dissolved in 30 μl of buffer containing 20 mM Tris.HCl pH 7.4, 7 mM $MgCl_2$, 60 mM NaCl, and 0.1 mg of BSA per ml and then digested with 10 U of HindIII endonuclease for 2 hr at 37° C. The reaction was terminated with 3 μl of 0.25M EDTA (pH 8.0) and 1.5 μl of 10% SDS and, after extraction with phenol-CHC13 followed by the addition of 30 μl of 4M ammonium acetate, the DNA was precipitated with 120 μl of ethanol. The pellet was rinsed with ethanol and then dissolved in 10 μl of 10 mM Tris.HCl (pH 7.3) and 1 mM EDTA, and 3 μl of ethanol was added to prevent freezing during storage at −20° C.

Step 4: Cyclization mediated by the oligo (dG)-tailed linker DNA

A 9 μl sample of the HindIII endonuclease-digested oligo (dC)-tailed cDNA:mRNA plasmid (about 90% of the sample) was incubated in a mixture (90 μl) containing 10 mM Tris.HCl pH 7.5, 1 mM EDTA, 0.1M NaCl, and 1.8 pmol of the oligo (dG)-tailed linker DNA at 65° C. for 5 min, shifted to 42° C. for 60 min, and then cooled to 0° C. The mixture (90 μl) was adjusted to a volume of 900 μl containing 20 mM Tris.HCl pH 7.5, 4 mM MgCl2, 10 mM $(NH_4)_2SO_4$, 0.1M KCl, 50 μg of BSA per ml, and 0.1 mM β-NAD; 6 μg of E. coli DNA ligase were added and the solution was then incubated overnight at 12° C.

Step 5: Replacement of RNA strand by DNA

To replace the RNA strand of the insert, the ligation mixture was adjusted to contain 40 μM of each of the four deoxynucleoside triphosphates, 0.15 mM β-NAD, 4 μg of additional E. coli DNA ligase, 16 U of E. coli DNA polymerase I (PolI,) and 9 U of E. coli RNase H. This mixture (960 μl) was incubated successively at 12° C. and room temperature for 1 hr each to promote optimal repair synthesis and nick translation by PolI.

Step 6: Transformation of E. coli

Transformation was carried out using minor modifications of the procedure described by Cohen et al. (Proc. Nat. Acad. Sci. U.S.A., 69: 2110–2114 [1972]). E. coli K-12 strain MC1061 (Casadaban, M. and Cohen, S., J. Mol. Biol. 138: 179–207 [1980]) was grown to 0.5 absorbancy unit at 600 nm at 37° C. in 20 ml of L-broth. The cells were collected by centrifugation, suspended in 10 ml of 10 mM Tris.HCl pH 7.3 containing 50 mM $CaCl_2$, and centrifuged at 0° C. for 5 min. The cells were resuspended in 2 ml of the above buffer and incubated again at 0° C. for 5 min.; then, 0.2 ml of the cell suspensions was mixed with 0.1 ml of the DNA solution (step 5) and incubated at 0° C. for 15 min. Next the cells were kept at 37° C. for 2 min. and thereafter at room temperature for 10 min.; then 0.5 ml of L-broth was added, and the culture was incubated at 37° C. for 30 min., mixed with 2.5 ml of L-broth soft agar at 42° C., and spread over L-broth agar containing 50 μg of ampicillin per ml. After incubation at 37° C. for 12 to 24 hr, individual colonies were picked with sterile tooth-picks. In all, approximately $1 \times 10^5$ independent cDNA clones were generated.

G. Size Fractionated Sub-library

30 μg of plasmid DNA representing the entire cDNA library (pcD-X DNA) was digested separately with the restriction enzymes SalI, HindIII, and ClaI to linearize the plasmid. The restricted DNAs were size-fractionated on a 1% agarose gel to separate plasmids having different size cDNA inserts. Segments were excised from the gel representing plasmids with cDNA inserts of the following size ranges:

0: −1 kb
1: −2 kb
2: −3 kb
3: −4 kb
4: −5 kb
5: kb and longer.

DNA was eluted from each gel slice using the glass powder method of Vogelstein and Gillespie (Proc. Nat. Acad. Sci. U.S.A., 76: 615–619 [1970]). The eluted DNAs from the 3 digests were pooled on the basis of size, and treated with T4 ligase to recyclize in a total volume of 15 μl containing 50 mM Tris.HCl pH 7.4, 10 mM MgCl2, 10 mM DTT, 1 mM spermidine, 1 mM ATP and 100 μg/ml BSA. The ligation reactions were incubated 16 hr at 12 C. About 3 μl of each combined size fraction was used to transform E. coli strain MC 1061 using the method of Cohen, S. et al. (Proc. Nat. Acad. Sci. U.S.A., 69: 2110–2114 [1972]). A library of about $10^5$ independent transformations was obtained for the fraction containing cDNA inserts 1–2 kb in length. A collection of $10^4$ independent clones were picked at random from the sublibrary enriched for cDNA inserts of 1–2 kb and propagated individually in wells of microtiter dishes containing 200 μl L broth with ampicillin at 50 μg/ml and dimethyl sulfoxide at 7%.

H. Screening of 1–2 kb Sub-library by DNA Transfections

Pools containing 48 cDNA clones were prepared from the microtiter cultures. 58 such pools were grown up in 1 liter cultures of L-broth containing 100 μg/ml ampicillin. Plasmid DNA was isolated from each culture and purified by twice banding through CsCl gradients. The DNA representing each pool was transfected into COS-7 monkey cells as follows.

One day prior to transfection, approximately $10^6$ COS-7 monkey cells were seeded onto individual 60 mm plates in DME containing 10% fetal calf serum and 2M glutamine. To perform the transfection, the medium was aspirated from each plate and replaced with 1.5 ml of DME containing 50 mM Tris.HCl pH 7.4, 400 μg/ml DEAE-Dextran and 15 μg of the plasmid DNAs to be tested. The plates were incubated for four hours at 37° C., then the DNA-containing medium was removed, and the plates were washed twice with 2 ml of serum-free DME. DME containing 150 μM chloroquine was added back to the plates which were then incubated for an additional 3 hrs at 37° C. The plates were washed once with DME and then DME containing 4% fetal calf serum, 2 mM glutamine, penicillin and streptomycin was added. The cells were then incubated for 72 hrs at 37° C. The growth medium was collected and assayed for murine IL-2 activity as described above.

Four pools (groups 6,33,40, and 56) yielded murine IL-2 activity (see Table II below). Group 33 was then subdivided into 8 pools, each containing 6 of the original pools. Only one of these subpools (group c) was positive in the transfection assay. Each of the plasmids in group c was transfected individually into COS-7 cells. Only one clone, designated MT-18, was active in producing TCGF activity.

Figure 2A:
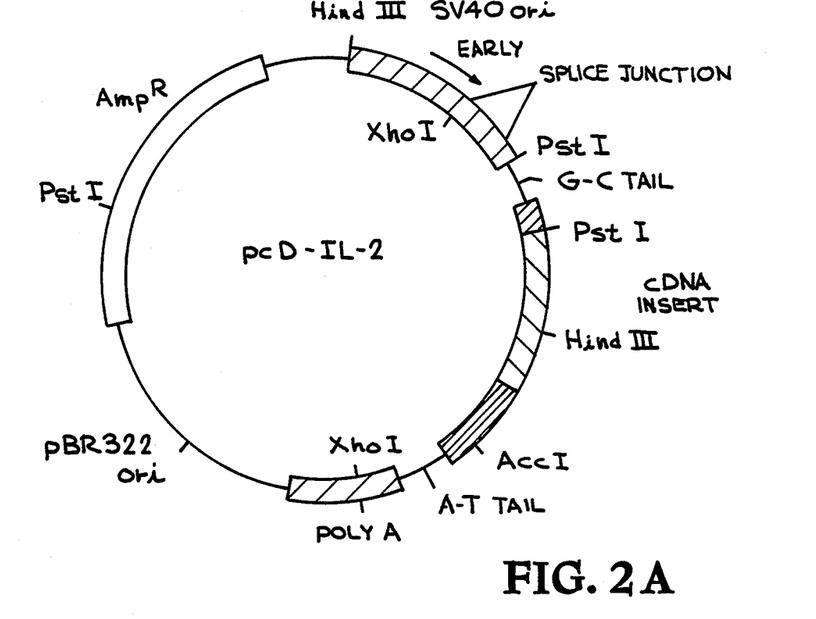
FIG. 2A illustrates pcD-IL-2, a plasmid carrying a cDNA clone exhibiting IL-2 activity.

Restriction mapping of the MT-18 cDNA clone identified a PstI-HindIII fragment within the cDNA insert, as shown in FIG. 2A. This fragment was purified by electrophoresis through a 5% poly acrylamide gel, and eluted. This fragment was labelled with $^{32}$P-dCTP by nick translation according to Maniatis, T. et al. ("Molecular Cloning, A Laboratory Manual", Cold Spring Harbor Laboratory, U.S.A. [1982]).

The pools of 48 cDNA clones were transformed from the microtiter trays to nitrocellulose filters placed on plates of L-agar+100 µg/ml ampicillin. These plates were incubated overnight at 37° C. The bacterial colonies were lysed and the DNA bound to the filters as described in Maniatis, T., et al. (above).

The nick translated PstI-HindIII fragment from MT-18 was hybridized with each of the 58 filters representing the pools. The hybridizations were performed in 6XSSPE (0.18M MaCl, 1 mM EDTA, and 10 mM NaH$_2$PO$_4$ [pH 7.9]), 50% formamide, 100 µg/ml E. coli tRNA, 0.1% SDS, at 42° C. overnight. The filters were washed once at room temperature in 2X SSPE 0.1% SDS, and then twice with 0.2X SSPE at 60° C. Following incubation of the filters, 15 individual clones were found to hybridize with the probe.

Plasmid DNA from each of these clones was prepared as described above, and transfected into COS-7 cells. Of these clones, only three, contained in pools 6 (MT-1), 40 (MT-20), and 56 (MT-28) produced high levels of murine IL-2 activity (see Table II). Restriction analysis showed that the clones share essentially the same structure.

TABLE II

| | DNA Transfection Assay for Murine IL-2 Activity from Pools of Plasmid DNA | | | | | |
|---|---|---|---|---|---|---|
| | DNA | units/ml | DNA | units/ml | DNA | units/ml |
| First screening | 1 | <10 | 21 | <10 | 41 | <10 |
| | 2 | <10 | 22 | <10 | 42 | <10 |
| | 3 | <10 | 23 | <10 | 43 | <10 |
| | 4 | <10 | 24 | <10 | 44 | <10 |
| | 5 | <10 | 25 | <10 | 45 | <10 |
| | 6 | 144 | 26 | <10 | 46 | <10 |
| | 7 | <10 | 27 | <10 | 47 | <10 |
| | 8 | <10 | 28 | <10 | 48 | <10 |
| | 9 | <10 | 29 | <10 | 49 | <10 |
| | 10 | <10 | 30 | <10 | 50 | <10 |
| | 11 | <10 | 31 | <10 | 51 | <10 |
| | 12 | <10 | 32 | <10 | 52 | <10 |
| | 13 | <10 | 33 | 128 | 53 | <10 |
| | 14 | <10 | 34 | <10 | 54 | <10 |
| | 15 | <10 | 35 | <10 | 55 | <10 |
| | 16 | <10 | 36 | <10 | 56 | 140 |
| | 17 | <10 | 37 | <10 | 57 | <10 |
| | 18 | <10 | 38 | <10 | 58 | <10 |
| | 19 | <10 | 39 | <10 | | |
| | 20 | <10 | 40 | 128 | | |
| Second screening: groups of six clones from group 33 | a | <10 | d | <10 | g | <10 |
| | b | <10 | e | <10 | h | <10 |
| | c | 1669 | f | <10 | | |
| Third screening: single clones from group C | 1 | <10 | 4 | <10 | | |
| | 2 | <10 | 5 | <10 | | |
| | 3(MT-18) | 9020 | 6 | <10 | | |
| Fourth screening: single clones hybridized with cDNA insert of clone MT-18 | MT-1 | 5851 | MT-7 | <10 | MT-22 | <10 |
| | MT-2 | <10 | MT-17 | <10 | MT-23 | <10 |
| | MT-3 | <10 | MT-19 | <10 | MT-26 | <10 |
| | MT-4 | <10 | MT-20 | 6800 | MT-28 | 8200 |
| | MT-5 | <10 | MT-21 | <10 | MT-29 | <10 |
| Mock-infected COS-7 | | <10 | | | | |

Figure 2B:
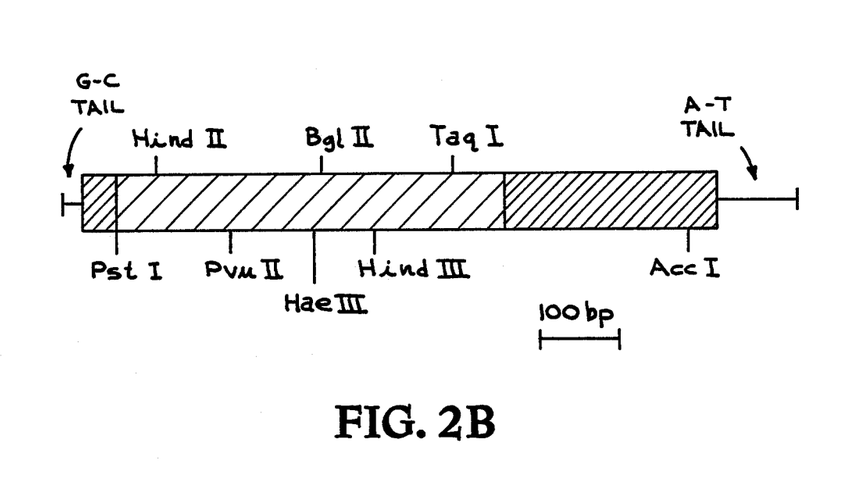
FIG. 2B is a restriction endonuclease cleavage map of the cDNA insert of FIG. 2A.

A plasmid (pcD-IL-2) carrying a substantially full-length cDNA insert is shown in FIG. 2, and an E. coli bacterium (MC1061) carrying the plasmid has been deposited with the ATCC (accession number 39892). In FIG. 2, transcription of the 816 bp cDNA insert contained in the pcD expression vector from the SV40 early promoter is indicated by the arrow. The locations of the splice donor and acceptor sites are shown. The polyadenylation signal, also derived from SV40, is located at the 3'-end of the cDNA insert. The IL-2 coding region in the cDNA insert is heavily shaded while the non-coding regions are lightly shaded. The remainder of the vector sequences are derived from pBR322, including the β-lactamase gene (Amp ®) and the origin of replication.

Figure 3:
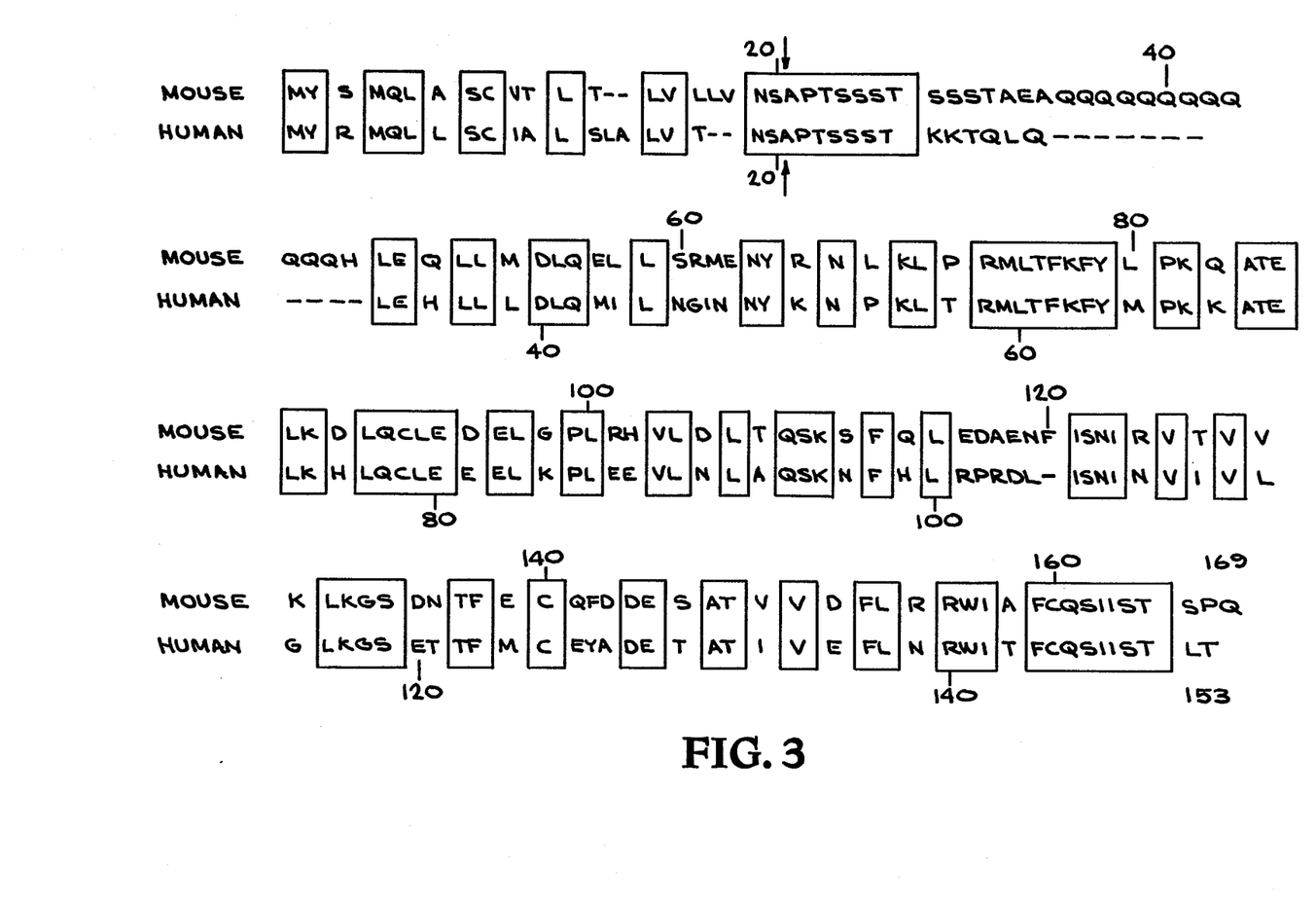
FIG. 3 represents a comparison between putative murine and human IL-2 amino acid sequences.

Utilizing both the M13 dideoxy chain termination method (Sanger, F., et al., Proc. Natl. Acad. Sci. U.S.A. 74: 5463–5467 [1977]) and modified Maxam/Gilbert technique (Rubin, C. and Schmid, C., Nucleic Acid Res. 8: 4613–4619 [1981]) and MT-1 sequence was determined. The cDNA insert contains a single open reading frame. The first ATG is found 49–51 nucleotides from the 5' end, and is followed by 168 codons before the termination triplet at nucleotide positions 553–555. FIG. 3 is a comparison between the putative mouse and human IL-2 protein sequences. Identical residues (after alignment) are shown in shaded boxes. Surprisingly, 89 of the prediced mouse IL-2 residues are conserved in human IL-2.

The homologies between the mouse IL-2 cDNA and human IL-2 cDNA are also surprising. Overall, there is about 70% homology between the two IL-2 cDNA sequences (Brutlag, D. et al., Nucleic Acids Res. 10: 279-294 [1981]). In particular, the regions covered by nucleotide positions 1-125, 229-354, and 416-680 share extensive homology with the corresponding regions of human IL-2 cDNA. However, the trinucleotide CAG sequence, which is repeated twelve times within the mouse IL-2 cDNA coding region, is not present in any human IL-2 cDNA isolated to date.

The clone library in the pcD expression vector enabled the identification of complete cDNA clones by direct expression in mammalian cells. Specifically, complete mouse IL-2 cDNA clones were directly identified by transfecting COS-7 cells with randomly picked cDNA clones, and measuring the TCGF activity secreted into the cell supernatant. These results indicate that the identification of full-length cDNA clones of lymphokines or hormones may be achieved solely on the basis of detection of a functional polypeptide in eukaryotic cells.

Identification of relevant cDNA clones based on the functional expression of the gene offers advantages to hybrid selection procedures. Identification of cDNA clones by hybrid selection relies on nucleotide sequence homology between mRNA and cDNA inserts, which can prove misleading. In fact, some of the functionally inactive cDNA clones which hybridized with the mouse IL-2 cDNA probe (MT-3, MT-4, MT-5, MT-7, MT-17, MT-19, MT-21, MT-22, MT-23, and MT-29 in Table II) have different restriction maps from that of the functional mouse IL-2 cDNA. Interestingly, these inactive clones also hybridized with a human IL-2 cDNA probe. Thus, it is possible to isolate irrelevant clones on the basis of partial sequence homology among the cDNA inserts. Furthermore, the cloning protocol disclosed herein is particularly useful in cases where the large amounts of mRNA needed for hybrid selection are not available.

From the foregoing, it will be appreciated that the cDNA clones of the present invention provide accurate and complete sequence data on murine IL-2. The invention also provides to those skilled in the art means for producing significant quantities of the factor (essentially free from other hematopoietic factors) for the improved in vitro maintenance of T cells and other hematopoietic cells. Further, the information gleaned from the cDNA clones increases understanding of the mammalian immune response, enhancing experimental research capabilities.

We claim:

1. A process for producing a polypeptide exhibiting murine interleukin-2 activity, said process comprising the steps of:
providing a vector comprising a nucleotide sequence coding for said polypeptide, wherein the nucleotide sequence is capable of being expressed by a host containing the vector and wherein the nucleotide sequence is selected from the group of nucleotide sequences capable of encoding a polypeptide having an amino acid sequence defined by the formula:

Ala—Pro—Thr—Ser—Ser—Ser—Thr—Ser—

-continued
Ser—Ser—Thr—Ala—Glu—Ala—Gln—Gln—
Gln—Gln—Gln—Gln—Gln—Gln—Gln—Gln—
Gln—Gln—His—Leu—Glu—Gln—Leu—Leu—
Met—Asp—Leu—Gln—Glu—Leu—Leu—Ser—
Arg—Met—Glu—Asn—Tyr—Arg—Asn—Leu—
Lys—Leu—Pro—Arg—Met—Leu—Thr—Phe—
Lys—Phe—Tyr—Leu—Pro—Lys—Gln—Ala—
Thr—Glu—Leu—Lys—Asp—Leu—Gln—Cys—
Leu—Glu—Asp—Glu—Leu—Gly—Pro—Leu—
Arg—His—Val—Leu—Asp—Leu—Thr—Gln—
Ser—Lys—Ser—Phe—Gln—Leu—Glu—Asp—
Ala—Glu—Asn—Phe—Ile—Ser—Asn—Ile—
Arg—Val—Thr—Val—Val—Lys—Leu—Lys—
Gly—Ser—Asp—Asn—Thr—Phe—Glu—Cys—
Gln—Phe—Asp—Asp—Glu—Ser—Ala—Thr—
Val—Val—Asp—Phe—Leu—Arg—Arg—Trp—
Ile—Ala—Phe—Cys—Gln—Ser—Ile—Ile—
Ser—Thr—Ser—Pro—Gln.

incorporating the vector into the host; and
maintaining the host containing the vector under conditions suitable for expression of the nucleotide sequence into said polypeptide.

2. The process of claim 1 wherein said host is a bacteria.

3. The process of claim 2 wherein said bacteria is *Escherichia coli*.

4. The process of claim 1 wherein said host is a eukaryotic cell.

5. The process of claim 4 wherein said eukaryotic cell is a yeast cell.

6. The process of claim 5 wherein said yeast cell is *Saccharomyces cerevisiae*.

7. The process of claim 6 wherein said vector is a plasmid comprising a 2 μm replication origin and a nucleotide sequence encoding an α-factor leader sequence.

8. The process of claim 7 wherein said vector is pMF-α8, deposited with the American Type Culture Collection under accession number 40140.

9. The process of claim 4 wherein said eukaryotic cell is a mammalian cell.

10. The process of claim 9 wherein said mammalian cell is selected from the group consisting of monkey cells and Chinese hamster cells.

11. The process of claim 10 wherein said vector comprises an SV40 origin of replication, an SV40 splice site, and an SV40 polyadenylation site.

12. The process of claim 11 wherein said vector is a pcD plasmid.

13. The process of claim 12 wherein said mammalian cell is a COS 7 monkey cell.

14. A nucleic acid having a nucleotide sequence capable of encoding a polypeptide having an amino acid sequence defined by the formula:

Ala—Pro—Thr—Ser—Ser—Ser—Thr—Ser—
Ser—Ser—Thr—Ala—Glu—Ala—Gln—Gln—
Gln—Gln—Gln—Gln—Gln—Gln—Gln—Gln—
Gln—Gln—His—Leu—Glu—Gln—Leu—Leu—
Met—Asp—Leu—Gln—Glu—Leu—Leu—Ser—
Arg—Met—Glu—Asn—Tyr—Arg—Asn—Leu—
Lys—Leu—Pro—Arg—Met—Leu—Thr—Phe—
Lys—Phe—Tyr—Leu—Pro—Lys—Gln—Ala—
Thr—Glu—Leu—Lys—Asp—Leu—Gln—Cys—
Leu—Glu—Asp—Glu—Leu—Gly—Pro—Leu—
Arg—His—Val—Leu—Asp—Leu—Thr—Gln—
Ser—Lys—Ser—Phe—Gln—Leu—Glu—Asp—
Ala—Glu—Asn—Phe—Ile—Ser—Asn—Ile—
Arg—Val—Thr—Val—Val—Lys—Leu—Lys—
Gly—Ser—Asp—Asn—Thr—Phe—Glu—Cys—
Gln—Phe—Asp—Asp—Glu—Ser—Ala—Thr—
Val—Val—Asp—Phe—Leu—Arg—Arg—Trp—

-continued
Ile—Ala—Phe—Cys—Gln—Ser—Ile—Ile—
　　　　　　　　　Ser—Thr—Ser—Pro—Gln.

15. An expression vector comprising a nucleotide sequence capable of encoding a polypeptide having an amino acid sequence defined by the formula:

Ala—Pro—Thr—Ser—Ser—Ser—Thr—Ser—
　　Ser—Ser—Thr—Ala—Glu—Ala—Gln—Gln—
　　Gln—Gln—Gln—Gln—Gln—Gln—Gln—Gln—
　　Gln—Gln—His—Leu—Glu—Gln—Leu—Leu—
　　Met—Asp—Leu—Gln—Glu—Leu—Leu—Ser—
　　Arg—Met—Glu—Asn—Tyr—Arg—Asn—Leu—
　　Lys—Leu—Pro—Arg—Met—Leu—Thr—Phe—

-continued
Lys—Phe—Tyr—Leu—Pro—Lys—Gln—Ala—
Thr—Glu—Leu—Lys—Asp—Leu—Gln—Cys—
Leu—Glu—Asp—Glu—Leu—Gly—Pro—Leu—
Arg—His—Val—Leu—Asp—Leu—Thr—Gln—
Ser—Lys—Ser—Phe—Gln—Leu—Glu—Asp—
　　Ala—Glu—Asn—Phe—Ile—Ser—Asn—Ile—
Arg—Val—Thr—Val—Val—Lys—Leu—Lys—
Gly—Ser—Asp—Asn—Thr—Phe—Glu—Cys—
Gln—Phe—Asp—Asp—Glu—Ser—Ala—Thr—
Val—Val—Asp—Phe—Leu—Arg—Arg—Trp—
Ile—Ala—Phe—Cys—Gln—Ser—Ile—Ile—
　　　　　　　　　Ser—Thr—Ser—Pro—Gln.

16. The expression vector of claim 45 consisting of pcD-II 2, deposited with the American Type Culture Collection under accession number 39892.

* * * * *